United States Patent [19]

Puffer et al.

[11] Patent Number: 4,705,957

[45] Date of Patent: Nov. 10, 1987

[54] WIRE SURFACE MONITOR

[75] Inventors: Leroy G. Puffer, Vernon; Robert K. Erf, Glastonbury, both of Conn.

[73] Assignee: United Technologies Corporation, Hartford, Conn.

[21] Appl. No.: 895,418

[22] Filed: Aug. 11, 1986

[51] Int. Cl.$^4$ .............................................. G01N 21/88
[52] U.S. Cl. .................................. 250/56 B; 250/572; 356/430
[58] Field of Search ............... 250/562, 563, 571, 572, 250/223 R, 228; 356/430

[56] References Cited

U.S. PATENT DOCUMENTS 4,095,905  6/1978  Kuni et al. ........................... 250/572
4,601,576  7/1986  Galbraith ............................. 356/430

Primary Examiner—David C. Nelms
Attorney, Agent, or Firm—Eric W. Petraske

[57] ABSTRACT

A non-contact optical detector for on-line inspection of the surface of a wire during manufacturing is improved by an azimuthally symmetric sensitivity and by a time-dependent response that permits discrimination among flaws of different magnitude.

6 Claims, 6 Drawing Figures

FIG. 3
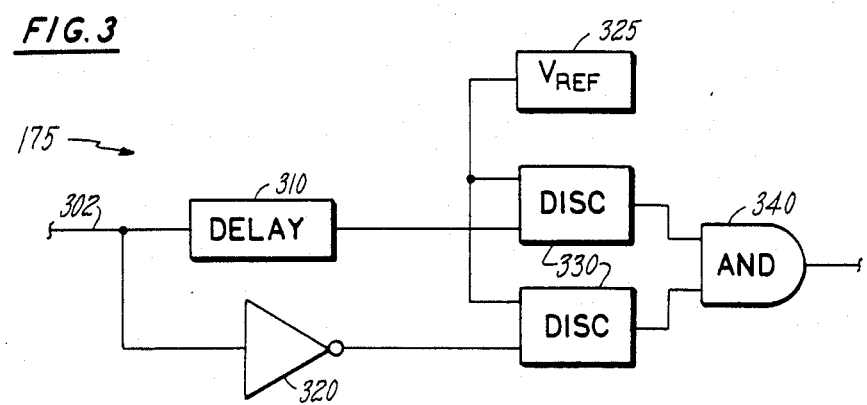
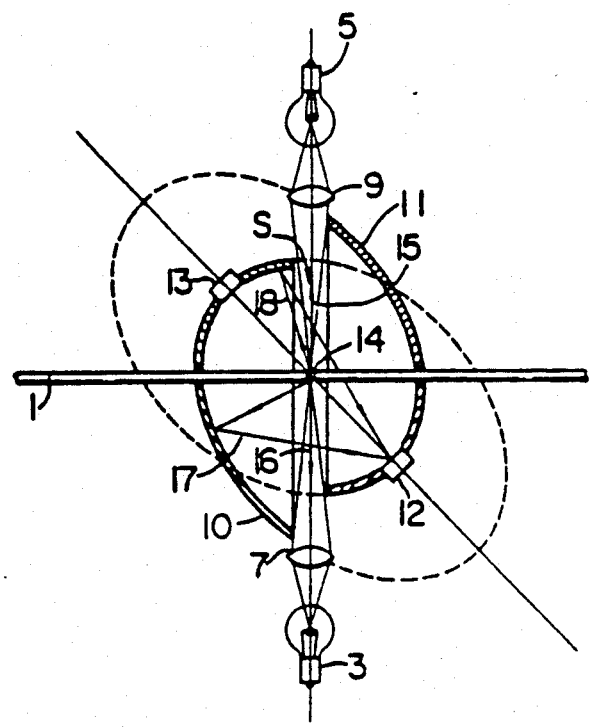
FIG. 4 PRIOR ART

WIRE SURFACE MONITOR

DESCRIPTION

1. Technical Field

The field of the invention is that of non-contact detection of surface flaws in wires.

2. Background Art

In the art of wire manufacturing, it is known to inspect the wire coating for surface flaws by means of a non-contact optical method in which light is scattered from a flaw in a different manner than it is scattered from a good area of the wire. The approach taken by Kuni et al in U.S. Pat. No. 4,095,905, is a compact device that is not, however, symmetric about the azimuth of the wire for small flaws on relatively large wires. This device, therefore, is subject to difficulty in detecting flaws in regions of the wire where the detector is insensitive and also in discriminating among flaws of different magnitude.

The problem addressed by this invention is that of a non-contact opto-electronic surface flaw detector that has a sensitivity that is substantially constant for all azimuthal angles of the wire.

DISCLOSURE OF INVENTION

The invention relates to an improved non-contact azimuthally symmetric optical detector for inspection of a wire that has an azimuthally symmetric path for radiation scattered from the wire.

A feature of the invention is the use of a relatively small non-planar mirror axially aligned with the wire together with a separate planar mirror for deflecting radiation away from the wire axis.

Another feature of the invention is substantially azimuthally symmetric sensitivity for both directly scattered radiation and radiation scattered indirectly through the non-planar mirror.

Another feature of the invention is the use of electronic circuits to discriminate in time between different types of flaws.

Another feature of the invention is the use of differential detection for improved noise rejection and flaw discrimination.

Yet another feature of the invention is the use of an optical system having lenses for gathering radiation from a relatively large area and focusing the radiation on a detecting device, thereby rendering the detecting device less sensitive to the alignment of the wire passing through and permitting the use of smaller non-planar mirrors for inspecting closely spaced arrays of wires.

BRIEF DESCRIPTION OF DRAWINGS

FIG. 3 illustrates an electronic detector circuit.

FIG. 4 illustrates a device in the prior art.

BEST MODE OF CARRYING OUT THE INVENTION

Figure 1A:
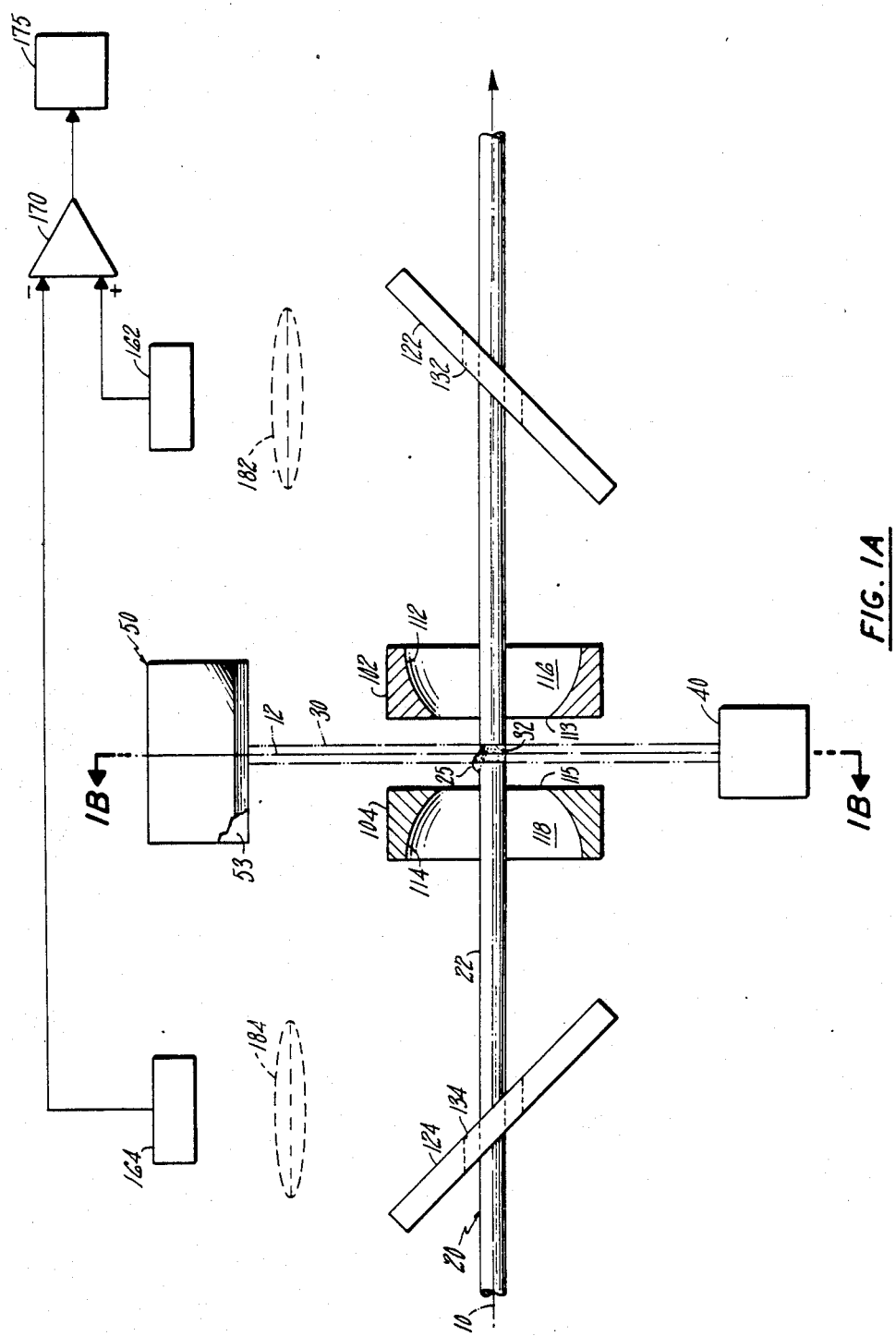
FIG. 1A illustrates in partially pictorial, partially schematic style, an illustrative embodiment of the invention.

FIG. 1A illustrates a cross section of a detecting device according to the invention. In this drawing, wire 20 travels along axis 10 horizontally in the figure, which axis 10 intersects vertical axis 12 at the center of the drawing. Along axis 12 passes a "light plane" 30 that is a substantially planar volume of radiation from radiation source 40, which may be a laser or any other convenient source for producing a generally planar beam of light. The region indicated by the numeral 32 on surface 22 of wire 20 is referred to as the illumination zone having an illumination zone length along axis 10. Radiation in light plane 30 is reflected by top mirror 50, so that the illumination of zone 32 is substantially azimuthally symmetric about axis 10. Wire 20 is indicated as traveling from left to right in the drawing. The left direction will be referred to as upstream and the right direction referred to as downstream in an obvious analogy. Mirror 50 is preferably placed above the wire, in part so that dirt will not drop onto the surface.

Radiation scattered from the illumination zone when the surface of wire 20 is smooth will generally be confined to light plane 30, with a small amount of specular radiation scattered to the left and right. Radiation scattered at a considerable angle, specular or scattered from a flaw, passes through two symmetric portions of the detecting apparatus as shown in the figure. The first elements are a pair of non-planar optical elements 102 and 104 having reflective surfaces 112 and 114 which collect radiation and direct it generally horizontally along the wire axis. Each surface has an aperture 113 or 115 for wire 20 to pass through. Preferably, each of surfaces 112 and 14 is a surface of revolution such as an ellipsoid or paraboloid for which the illumination zone is at one focus. The volumes 116 and 118 in the interior of these surfaces will be referred to as the "reflective volume" for that surface. Both the radiation directly scattered and that scattered off the non-planar reflective surface are deflected upward in the drawing by a pair of planar mirrors 122 and 124 having respective apertures 132 and 134 for the wire to pass through. The radiation deflected by mirrors 122 and 124 is detected by optical detectors 162 and 164 that are positioned above the plane of the wire. If surfaces 112 and 114 are ellipsoidal, then detectors 162 and 164 will be placed at the opposite focus of the respective ellipsoid.

This figure has been drawn with blocks 102 and 104 separated by an exaggerated amount in order to present the construction clearly. The spacing between the reflective elements, their mounting and the like are matters of design choice.

Figure 1B:
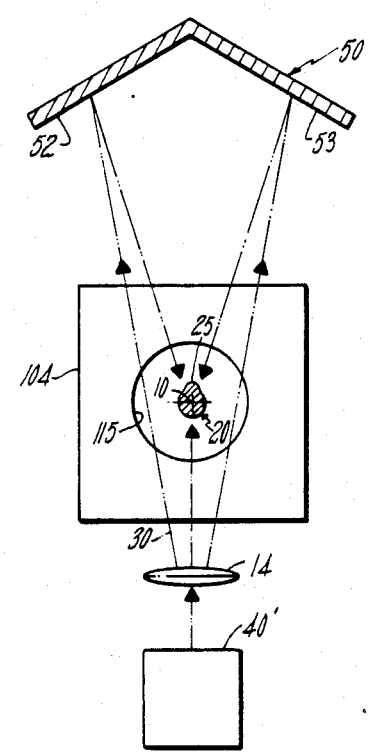
FIG. 1B shows a cross section of the embodiment of FIG. 1A.

Referring now to FIG. 1B, there is shown a cross section taken along the line 1B—1B of FIG. 1A perpendicular to the plane of FIG. 1A and passing through axis 12. Axis 10 in this figure is drawn perpendicular to the plane of the paper and about it is shown a cross section of wire 20, aperture 115 and a cross section of top mirror 50. Radiation in light plane 30 travels generally upward in this figure coming from cylindrical lens 14 that produces a slightly diverging beam that has the thickness of the illumination zone perpendicular to the plane of the paper and covers a sufficiently large area to intercept mirror 50. The remainder of the illumination system is shown as box 40'.

Mirror 50 has reflecting surfaces 52 and 53 that are each at an angle of approximately 60 degrees with respect to axis 12 to illuminate the upper two thirds of wire 20. Wire 20 will thus be substantially evenly illuminated about an azimuthal angle in the plane of the paper extending all around the surface of the wire. The relative intensity of the illumination of the top of the wire can be adjusted to compensate for lost scattered radiation which is intercepted and deflected out of the system by relatively large wires. It will readily be apparent on inspection of FIGS. 1A and 1B that detector 162 will "see" essentially the view shown in FIG. 1B, as though it were located on axis 10. The sensitivity of detector 162 is thus uniform for all azimuthal angles of wire 20 about axis 10. Detector 164 also has a symmetric sensitivity since the left half of the apparatus is the mirror image of the right half.

Figure 2:
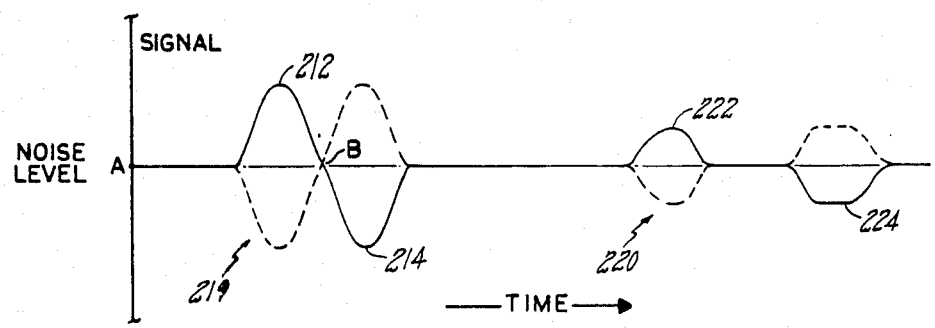
FIG. 2 shows a diagram of signals produced by the detecting device.

Referring back now to FIG. 1A, signals from conventional detectors 162 and 164 enter differential amplifier 170 to produce an output signal that goes to an electronics module indicated schematically by a box labeled with the numeral 175. The development of a flaw signal in time is relevant to the operation of this device and will now be explained with the aid of FIGS. 1A and 2. Flaw 25 is shown as entering light plane 30 from the left. If the thickness of light plane 30 (the illumination zone length) is less than or equal to the width of flaw 25, then radiation will first be scattered to the right, both directly and off surface 112 and will enter detector 162 before any substantial amount of radiation reaches detector 164 on the left. The reason is that the angle of reflection will direct the scattered radiation to the right. The signal in this case is illustrated by the solid line in region 219 of FIG. 2, in which a horizontal line at point A on the vertical axis represents the steady state noise level produced by background scattered radiation. A first region 212 represents the net signal from amplifier 170 and has a positive peak resulting from the signal received first in time by detector 162. When the top portion of flaw 25 is centered on axis 12, radiation will be scattered symmetrically, as can readily be seen in FIG. 1A, to both detectors 162 and 164. The signals from both these detectors will thus cancel, producing a net zero signal at point B relative to the noise level A. As flaw 25 passes to the right out of light plane 30, detector 162 will have less signal and the signal from detector 164 will become dominant, as is shown by the solid line in region 214. The signal from amplifier 70 thus has an amplitude dependence that indicates a flaw and also a time dependence. If the width of flaw 25 is approximately equal to the width of the illumination zone along the wire, then the signal will have the form shown in region 219 in which the signal drops to zero and passes immediately below. If, however, the width of flaw 25 is greater than the width of light plane 30, then there will be a longer period in which radiation is substantially equally deflected into both detectors. This example is shown by the solid line in region 220 for a flaw that has a substantially flat area on the top (or is substantially uniform) for a length along wire 20 that is large compared to the width of light plane 30. In that case, signals from detectors 162 and 164 will cancel for a relatively long time producing two displaced signals 222 and 224. There is thus an additional ability provided by this apparatus, in that both amplitude and time may be used to discriminate among signals characteristic of different flaws.

If the flaw is transparent, as is the case with some wire coating materials, then radiation will first be scattered to the left off of surface 114 and will enter detector 164 before any substantial amount of radiation reaches detector 162 on the right. The reason is that the illuminating radiation is refracted and reflected within the flaw rather than reflected at its surface, thereby directing the scattered radiation to the left. The signal in this case is illustrated by the dashed line in region 219 of FIG. 2 for small flaws. For larger flaws the signal is illustrated by the dashed line in region 220 of FIG. 2.

It is instructive to contrast the prior art device of FIG. 4, in which a wire 1 travels horizontally and passes through two ellipsoidal partial surfaces, 10 on the left and 11 on the right. It is readily apparent that this device is not symmetric about the azimuth of the wire. For example, detector 12 in the lower right hand corner will be strongly responsive to flaws on the top of wire 1, where scattered radiation along path 18 is directed efficiently at a near normal angle onto detector 12, and considerably less responsive to flaws on the bottom, where scattered radiation along path 17 is directed inefficiently at a skewed angle onto detector 12. In addition, radiation reflected from the top of wire 1 will be directed directly at detector 13 while also reflected from the surface of ellipsoid 10 to detector 12, thereby nullifying the differential detection scheme.

Detectors 12 and 13 respond with uniform sensitivity only for flaws on the sides of the wire. Both of these detectors are strongly sensitive to direct radiation in an azimuthally asymmetric fashion, so that the response of the total system will also be strongly dependent on the azimuthal angle. This azimuthal dependence is further aggravated by the use in other embodiments of the prior art system of a lower mirror generally similar to mirror 50 of this invention but placed close to the wire where it will obstruct scattered radiation over a large solid angle. The detector system of this prior art device uses a relatively wide illuminating light beam and produces only a pulse of one polarity for a detection signal and thus is not able to use discrimination in time to discriminate among different flaws.

Referring now to FIG. 3, there is illustrated a simplified portion of electronics module 175, illustrating pulse discrimination using time. Wire 302 carries the signal from amplifier 170 to both delay circuit 310 and inverter 320. Other conventional electronics not shown processes the main flaw detector signal from amplifier 170. Two matched discriminators 330 compare a positive voltage threshold signal from circuit 325 with the incoming signal. When the input signal is greater than the threshold, circuit 310 puts out a positive standard extended pulse. In the case of a signal such as that shown in area 220 of FIG. 2, the delay in circuit 310 is set to be approximately equal to the threshold delay expected of some threshold flaw length as it passes light plane 30. Thus, the signal 222 and the inverted signal 224 will both trigger discriminators 330 and pass to AND gate 340 at the same time, when a flaw of the size characteristic of delay 310 or greater than that size passes through light plane 30. If the flaw is smaller in size than that threshold length, then the signal 212 that passes through delay line 310 will be out of time with the signal from inverter 320 when it reaches AND gate 340 and AND gate 340 will thus not respond. Both the voltage reference from circuit 325 and the delay in circuit 310 will be set at predetermined values during calibration of the apparatus, of course. They will both depend on the size of the flaws, the size of the wire, the reflectivity/refraction of the wire coating material, and the usual number of other considerations. For transparent flaws a negative voltage threshold signal and a negative standard extended pulse would be used.

This device, then, has through a combination of improved geometry and electronics produced an azimuthally symmetric sensitivity to flaws at all positions of the wire and an improved ability to discriminate among flaws of different sizes.

Referring again to FIG. 1A, there is shown in dotted line two lenses 182 and 184. In an alternative embodiment of the invention, surfaces 112 and 114 will be paraboloids with illumination zone 32 at the foci. As is known, the paraboloids will produce a substantially collimated output beam that is deflected by mirrors 122 and 124. Lenses 182 and 184 will then focus that beam onto detectors 162 and 164. Detectors 162 and 164 will be sufficiently large to receive the focused image of a flaw at any position on the surface on the wire 20. This alternative embodiment is better suited for relatively large wires and is also more tolerant of the vibration and variation in position of wire 20 as it passes through the detecting system.

Figure 5:
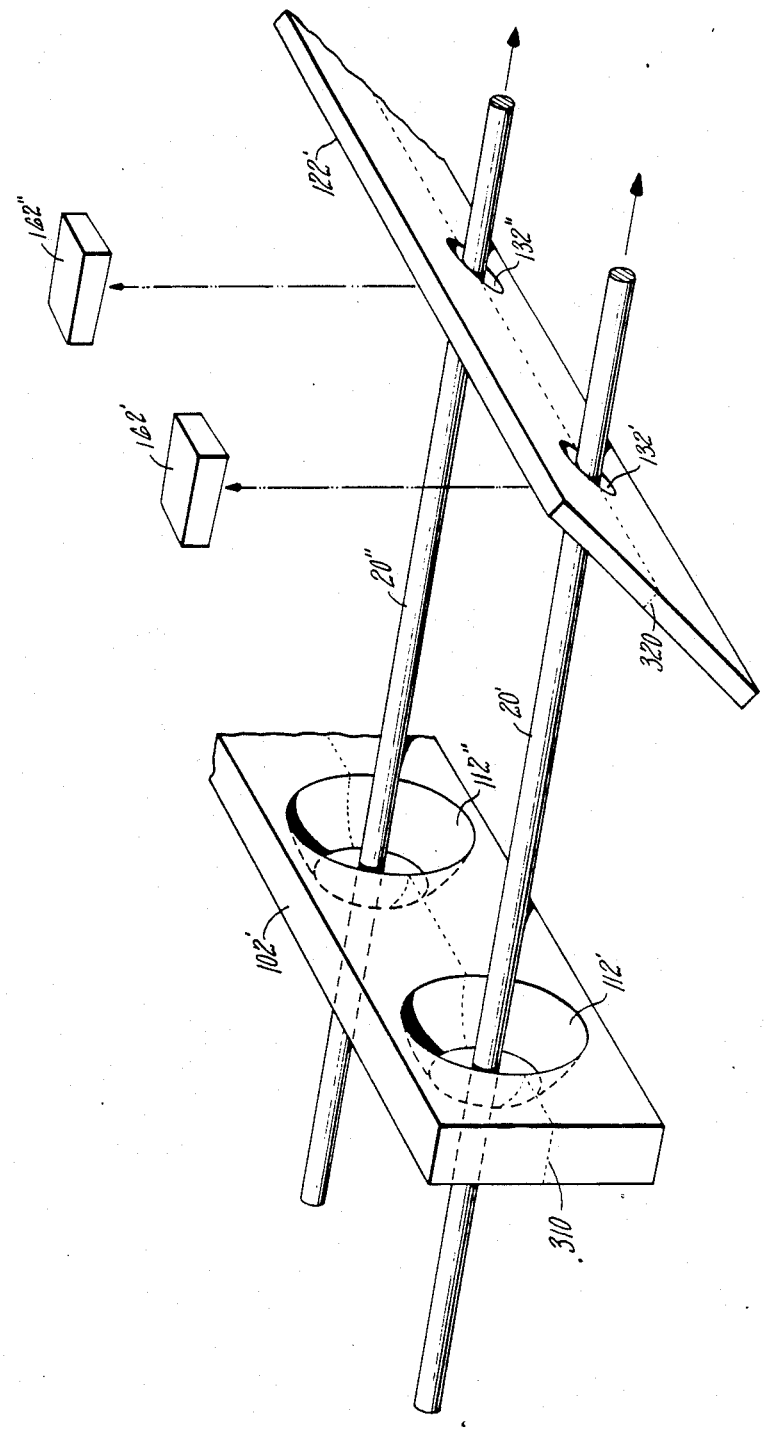
FIG. 5 illustrates an alternate embodiment of the invention.

Wire coating machines commonly handle a number of wires in parallel. FIG. 5 illustrates a portion of an alternative embodiment of the invention showing two wires 20' and 20" passing through a block 102' having non-planar surfaces 112' and 112". At a distance that is exaggerated for clarity, mirror 122', having apertures 132' and 132" deflects radiation upward toward detectors 162' and 162". The number of wires can be increased as desired. The left hand side of the figure is symmetric and has been omitted from the drawing in order to improve the clarity of presentation.

Dotted lines 310 and 320 indicate that the device may be constructed in two separable portions for convenience in mounting on-line without the need to thread the wires through the device. The embodiment of FIG. 1 may also be constructed in a separable fashion.

We claim:

1. A surface-defect detection device for identifying the presence of defects on the surface of a wire traveling along an axis from an upstream direction toward a downstream direction and comprising:
    light means for illuminating an azimuthal zone of said wire having a predetermined illumination zone length along said axis;
    at least two light reflecting means having a non-planar reflective surface disposed on upstream and downstream sides of said illumination zone;
    at least two radiation detectors disposed to receive radiation reflected from defects on said surface of said wire and to emit signals having a signal magnitude related to the magnitude of scattered radiation; and
    electronic means for combining signals from said radiation detectors to produce a flaw detection signal; characterized in that:
    said non-planar reflective surfaces are azimuthally symmetric about said axis and each define a reflective volume in an interior portion thereof;
    said at least two radiation detectors are disposed outside said reflective volumes and at a predetermined distance from said illumination zone; and
    said device further includes upstream and downstream azimuthally symmetric reflective surfaces positioned along said axis and having an aperture for the passage of said wire therethrough, oriented to direct toward a corresponding radiation detector both radiation scattered directly from a surface defect and radiation that is first scattered from said surface defect and then is reflected from a corresponding one of said non-planar reflective surfaces, whereby said radiation detectors are substantially equally responsive to surface flaws in all azimuthal positions of said wire.

2. A device according to claim 1, further characterized in that said non-planar reflective surfaces reflect scattered radiation from said illumination zone into at least two substantially collimated beams and in that at least two lenses disposed to intercept said beams focus said beams onto said radiation detectors in at least two beam spots smaller in area than the area of said radiation detectors.

3. A device according to claim 1, further characterized in that said electronic means for combining signals from said radiation detectors includes both means responsive to said signal magnitudes of said signals from said radiation detectors and also includes means responsive to the relationship in time of said signals from said radiation detectors.

4. A device according to claim 3, further characterized in that said electronic means for combining signals from said radiation detectors includes means for rejecting signals in which a delay time between a first and a second signal from a corresponding first and second detector is less than a predetermined threshold delay, whereby said device may be set to ignore flaws of less than a predetermined magnitude.

5. A device according to claim 1, further characterized in that said device is adapted to detect defects on at least two wires by further including;
    at least two light reflecting means per wire; and
    at least two radiation detectors per wire.

6. A device according to claim 5, further characterized in that at least two of said wires are illuminated by a common light source.

* * * * *